;(12) United States Patent
Tetarenko et al.

(10) Patent No.: US 9,428,816 B2
(45) Date of Patent: *Aug. 30, 2016

(54) METHOD OF TREATING ETHANOL PRODUCTION BYPRODUCTS (71) Applicant: SHELL OIL COMPANY, Houston, TX (US)

(72) Inventors: Pamela Karen Tetarenko, League City, TX (US); Paul Richard Weider, Houston, TX (US); Robert Lawrence Blackbourn, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/715,311

(22) Filed: Dec. 14, 2012

(65) Prior Publication Data

US 2013/0157333 A1    Jun. 20, 2013

Related U.S. Application Data (60) Provisional application No. 61/570,917, filed on Dec. 15, 2011.

(51) Int. Cl.
| | |
|---|---|
| *C13K 13/00* | (2006.01) |
| *C12P 7/14* | (2006.01) |
| *C12P 7/08* | (2006.01) |
| *C12P 7/10* | (2006.01) |
| *C12P 7/06* | (2006.01) |
| *C13K 1/02* | (2006.01) |

(52) U.S. Cl.
CPC . *C13K 13/00* (2013.01); *C12P 7/06* (2013.01); *C12P 7/08* (2013.01); *C12P 7/10* (2013.01); *C12P 7/14* (2013.01); *C13K 1/02* (2013.01); *C13K 13/002* (2013.01); *C12P 2201/00* (2013.01); *C12P 2203/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 3,549,319 | A | * | 12/1970 | Das et al. .................. 423/519 |
| 5,536,325 | A | | 7/1996 | Brink |
| 5,789,210 | A | | 8/1998 | Ho et al. |
| 6,475,768 | B1 | | 11/2002 | Otero et al. |
| 7,781,191 | B2 | | 8/2010 | Dunson, Jr. et al. |
| 2003/0162271 | A1 | | 8/2003 | Zhang et al. |
| 2008/0216391 | A1 | | 9/2008 | Cortright et al. |
| 2011/0154721 | A1 | | 6/2011 | Chheda et al. |
| 2011/0282115 | A1 | | 11/2011 | Chheda et al. |
| 2012/0122152 | A1 | | 5/2012 | Blackbourn et al. |
| 2013/0196400 | A1 | | 8/2013 | Weider et al. |

FOREIGN PATENT DOCUMENTS

| | | |
|---|---|---|
| EP | 863901 | 10/2003 |
| EP | 1727890 | 5/2008 |
| WO | 9513362 | 5/1995 |
| WO | 2005079193 | 9/2005 |
| WO | WO 2005079193 A2 * | 9/2005 |
| WO | 2005093041 | 10/2005 |
| WO | 2006096130 | 9/2006 |
| WO | 2007028811 | 3/2007 |
| WO | 2008119082 | 10/2008 |
| WO | 2009109631 | 9/2009 |
| WO | 2010015404 | 2/2010 |
| WO | WO 2010015404 A1 * | 2/2010 |

OTHER PUBLICATIONS

Brownwell HH et al. Steam Pretreatment of Lignocellulosic Material for Enhanced Enzymatic Hydrolysis. 1987. Biotechnology and Bioengineering. vol. XXIX. pp. 228-235.*
International Search Report dated Mar. 4, 2013 for Reference No. TH4179-PCT, Application PCT/US2012/069424 filed Dec. 13, 2012.
Brown, Robert C. et al; "Fast Pyrolysis and Bio-oil Upgrading", Pacific Northwest National Laboratory, Richland, Washington, Sep. 5-6, 2006.
Ingledew, W.M. et al.; "The Alcohol Industry: How Has It Changed and Matured?", The Alcohol Textbook, Ethanol Technology Institute, 2009, Fifth Ed., Chapter 1, pp. 1-175.

\* cited by examiner

*Primary Examiner* — Paul Holland (57) ABSTRACT

A method of treating ethanol production byproduct is provided by treating wet distillers grain or stillage with a solution containing at least one α-hydroxysulfonic acid to produce at least one fermentable sugar containing product. Fermentable sugar useful for the production of biofuels or ethanol can be produced from such methods. The α-hydroxysulfonic acid can be easily removed from the product and recycled.

27 Claims, 5 Drawing Sheets

METHOD OF TREATING ETHANOL PRODUCTION BYPRODUCTS

The present application claims the benefit of U.S. Provisional Patent Application Ser. No. 61/570,917, filed Dec. 15, 2011, the entire disclosure of which is hereby incorporated by reference.

FIELD OF THE INVENTION

The invention relates to a process for treating ethanol byproducts, more specifically wet distiller's grains or stillage, to produce sugars and/or alcohols.

BACKGROUND OF THE INVENTION

Distiller's grains are a byproduct from brewers and ethanol plants. Wet distiller grains are a primary byproduct of the 1st generation corn ethanol industry. In a dry mill process, the entire grain kernel is ground (milled) into flour. The flour is physically and chemically prepared for fermentation via cooking to produce a mash and the mash is hydrolyzed to release the sugars using enzymatic saccharification. The sugar mixture, with solids, is then fermented to produce ethanol. The fermented product is distilled to separate ethanol from the unconverted solids and process water as stillage from the bottom of the distillation tank. In a typical process whole stillage is separated into thin stillage (liquid fraction) and a solid fraction known as wet distillers grain.

Wet distillers grains (WDG) contains primarily unfermented grain residues (protein, fiber, fat) and up to 70 percent moisture. WDG has a short shelf life (a week or less) and transportation involves movement of high water weight. WDG supply transport is economically viable usually within a 200 km radius from the ethanol production facility. These facts are important as they affect both profitability and logistic issues. WDG can be dried to produce Dry Distiller Grains which can be optionally combined with concentrated thin stillage (heavy syrup) to produce dried distillers grains with solubles (DDGS). DDGS is an animal feed that has an almost indefinite shelf life and may be sold and shipped to any market. Drying is costly, both from a capital and energy point of view, according to a recent article (Ryan C. Christiansen "DDGS: Supplying Demand" Ethanol Producer Magazine, March 2009) up to 30% of the operating budget in a modern first generation dry-grind ethanol facility being used to produce dry distiller grains with solubles. As a result this commodity product represents little overall value to the corn mill. WDG contains sugars in the form of unconverted polysaccherides such as cellulose, hemicellulose, and starch within the fibers. Thus conversion of these latent sugars into additional ethanol represents a value added stream for a $1^{st}$ generation ethanol plant.

A primary obstacle to the usage of the fiber in WDG is an expensive "pretreatment" step to release these sugars and make the cellulose and other polysaccharides in the feedstock accessible to enzymatic hydrolysis. One of the leading candidates for such a pretreatment is dilute mineral acid hydrolysis (typically sulfuric or hydrochloric acid). The conditions of a successful pretreatment in dilute acid hydrolysis are determined by a combination of three factors; time, temperature, and acid concentration. Increased temperatures lead to loss of sugars to degradation products and increasing acid concentration (to lower the temperature) comes at the expense of the acid employed and neutralized salts in downstream equipment.

SUMMARY OF THE INVENTION

Given the above information, it is desirable to utilize the fiber in WDG or stillage within its shelf life by employing an effective and improved "pretreatment" step to make the polysaccharides in the non-fermentable residue from alcohol production process accessible to subsequent utilization, via direct hydrolysis and/or enzymatic hydrolysis to produce sugars for further conversion to fuels.

In an embodiment, a method of treating ethanol production byproduct is provided comprising: (a) providing a wet distillers grain; and (b) contacting the wet distillers grain with a solution containing at least one α-hydroxysulfonic acid thereby hydrolyzing the wet distillers grain to produce at least one fermentable sugar containing product.

In yet another embodiment, a method of treating ethanol production byproduct is provided comprising: (a) providing a wet distillers grain; (b) contacting the wet distillers grain with a solution containing at least one α-hydroxysulfonic acid thereby hydrolyzing the wet distillers grain to produce at least one fermentable sugar containing product, and (c) removing the α-hydroxysulfonic acid from the product by heating and/or reducing pressure to produce an acid-removed product containing at least one fermentable sugar substantially free of the α-hydroxysulfonic acid.

In another embodiment, a method comprises recycling the removed α-hydroxysulfonic acid to step (b) as components or in its recombined form.

In yet another embodiment, a method comprises fermenting a stream containing sugars produced by the above methods.

In yet another embodiment, a method is provided comprising: (a) providing grain; (b) grinding said grain to produce ground grain; (c) treating said ground grain to produce a fermentable sugar mixture; (d) fermenting the fermentable sugar mixture to produce a product containing ethanol, solids and water; (e) separating said fermented product to produce ethanol and stillage; and (f) contacting at least a portion of the stillage with a solution containing at least one α-hydroxysulfonic acid thereby hydrolyzing the stillage to produce at least one fermentable sugar containing product.

In yet another embodiment, a method is provided comprising: (a) providing grain; (b) grinding said grain to produce ground grain; (c) treating said ground grain to produce a fermentable sugar mixture; (d) fermenting the fermentable sugar mixture to produce a product containing ethanol, solids and water; (e) separating said fermented product to produce ethanol and stillage; (f) separating stillage to produce thin stillage and wet distillers grain; and (g) contacting at least a portion of the wet distillers grain with a solution containing at least one α-hydroxysulfonic acid thereby hydrolyzing the wet distiller grains to produce at least one fermentable sugar containing product.

The features and advantages of the invention will be apparent to those skilled in the art. While numerous changes may be made by those skilled in the art, such changes are within the spirit of the invention.

BRIEF DESCRIPTION OF THE DRAWING

This drawing illustrates certain aspects of some of the embodiments of the invention, and should not be used to limit or define the invention.

DETAILED DESCRIPTION OF THE INVENTION

It has been found that the present invention provides an improved method for the acid treatment of wet distillers grain or stillage to produce sugars and biofuels. The α-hydroxysulfonic acid is effective for treatment of hydrolyzing the wet distillers grain or stillage to fermentable sugars like pentose such as xylose at lower temperature, e.g., about 110° C. for α-hydroxymethane sulfonic acid or α-hydroxyethane sulfonic acid, producing little to no furfural in the process. Further, the α-hydroxysulfonic acid is reversible to readily removable and recyclable materials unlike mineral acids such as sulfuric, phosphoric, or hydrochloric acid. The process produces significant amounts of glucose in addition to xylose such that a subsequent hydrolysis by other conventional methods (e.g., enzyme hydrolysis) may not be necessary. The alpha-hydroxysulfonic acids of the general formula where $R_1$ and $R_2$ are individually hydrogen or hydrocarbyl with up to about 9 carbon atoms that may or may not contain oxygen can be used in the treatment of the instant invention. The alpha-hydroxysulfonic acid can be a mixture of the aforementioned acids. The acid can generally be prepared by reacting at least one carbonyl compound or precursor of carbonyl compound (e.g., trioxane, paraformaldehyde, metaldehyde, etc.) with sulfur dioxide or precursor of sulfur dioxide (e.g., sulfur and oxidant, or sulfur trioxide and recuing agent) and water according to the following general equation 1.

where $R_1$ and $R_2$ are individually hydrogen or hydrocarbyl with up to about 9 carbon atoms or a mixture thereof.

Illustrative examples of carbonyl compounds useful to prepare the alpha-hydroxysulfonic acids used in this invention are found where
$R_1=R_2=H$ (formaldehyde)
$R_1=H, R_2=CH_3$ (acetaldehyde)
$R_1=H, R_2=CH_2CH_3$ (propionaldehyde)
$R_1=H, R_2=CH_2CH_2CH_3$ (n-butyraldehyde) $R_1=H, R_2=CH(CH_3)_2$ (i-butyraldehyde)
$R_1=H, R_2=CH_2OH$ (glycolaldehyde)
$R_1=H, R_2=CHOHCH_2OH$ (glyceraldehdye)
$R1=H, R2=C(=O)H$ (glyoxal)

$R_1=R_2=CH_3$ (acetone)
$R_1=CH_2OH, R_2=CH_3$ (acetol)
$R_1=CH_3, R_2=CH_2CH_3$ (methyl ethyl ketone)
$R_1=CH_3, R_2=CHC(CH_3)_2$ (mesityl oxide)
$R_1=CH_3, R_2=CH_2CH(CH_3)_2$ (methyl i-butyl ketone)
$R_1, R_2=(CH_2)_5$ (cyclohexanone) or
$R_1=CH_3, R_2=CH_2Cl$ (chloroacetone)

The carbonyl compounds and its precursors can be a mixture of compounds described above. For example, the mixture can be a carbonyl compound or a precursor such as, for example, trioxane which is known to thermally revert to formaldehyde at elevated temperatures or an alcohol that maybe converted to the aldehyde by dehydrogenation of the alcohol to an aldehyde by any known methods. An example of such a conversion to aldehyde from alcohol is described below. An example of a source of carbonyl compounds maybe a mixture of hydroxyacetaldehyde and other aldehydes and ketones produced from fast pyrolysis oil such as described in "Fast Pyrolysis and Bio-oil Upgrading, Biomass-to-Diesel Workshop", Pacific Northwest National Laboratory, Richland, Wash., Sep. 5-6, 2006. The carbonyl compounds and its precursors can also be a mixture of ketones and/or aldehydes with or without alcohols that may be converted to ketones and/or aldehydes, preferably in the range of 1 to 7 carbon atoms.

The preparation of α-hydroxysulfonic acids by the combination of an organic carbonyl compounds, $SO_2$ and water is a general reaction and is illustrated in equation 2 for acetone.

The α-hydroxysulfonic acids appear to be as strong as, if not stronger than, HCl since an aqueous solution of the adduct has been reported to react with NaCl freeing the weaker acid, HCl (see U.S. Pat. No. 3,549,319). The reaction in equation 1 is a true equilibrium, which results in facile reversibility of the acid. That is, when heated, the equilibrium shifts towards the starting carbonyl, sulfur dioxide, and water (component form). If the volatile components (e.g. sulfur dioxide) is allowed to depart the reaction mixture via vaporization or other methods, the acid reaction completely reverses and the solution becomes effectively neutral. Thus, by increasing the temperature and/or lowering the pressure, the sulfur dioxide can be driven off and the reaction completely reverses due to Le Châtelier's principle, the fate of the carbonyl compound is dependant upon the nature of the material employed. If the carbonyl is also volatile (e.g. acetaldehyde), this material is also easily removed in the vapor phase. Carbonyl compounds such as benzaldehyde, which are sparingly soluble in water, can form a second organic phase and be separated by mechanical means. Thus, the carbonyl can be removed by conventional means, e.g., continued application of heat and/or vacuum, steam and nitrogen stripping, solvent washing, centrifugation, etc. Therefore, the formation of these acids is reversible in that as the temperature is raised, the sulfur dioxide and/or aldehyde and/or ketone can be flashed from the mixture and condensed or absorbed elsewhere in order to be recycled. It has been found that these reversible acids, which are approximately as strong as strong mineral acids, are effective in WDG or stillage treatment reactions. We have found that these treatment reactions produce very few of the undesired byproducts, furfurals, produced by other conventional mineral acids. Additionally, since the acids are effectively removed from the reaction mixture following treatment, neutralization with base and the formation of salts to complicate downstream processing is substantially avoided. The ability to reverse and recycle these acids also allows the use of higher concentrations than would otherwise be economically or environmentally practical. As a direct result, the temperature employed in WDG or stillage treatment can be reduced to diminish the formation of byproducts such as furfural or hydroxymethylfurfural.

It has been found that the position of the equilibrium given in equation 1 at any given temperature and pressure is highly influenced by the nature of the carbonyl compound employed, steric and electronic effects having a strong influence on the thermal stability of the acid. More steric bulk around the carbonyl tending to favor a lower thermal stability of the acid form. Thus, one can tune the strength of the acid and the temperature of facile decomposition by the selection of the appropriate carbonyl compound.

In one embodiment, the acetaldehyde starting material to produce the alpha-hydroxysulfonic acids can be provided by converting ethanol, produced from the fermentation of the treated WDG or stillage of the invention process, to acetaldehyde by dehydrogenation or oxidation. Dehydrogenation may be typically carried out in the presence of copper catalysts activated with zinc, cobalt, or chromium. At reaction temperatures of about 260-290° C., the ethanol conversion per pass is 30-50% and the selectivity to acetaldehyde is between 90 and 95 mol %. By-products include crotonaldehyde, ethyl acetate, and higher alcohols. Acetaldehyde and unconverted ethanol are separated from the exhaust hydrogen-rich gas by washing with ethanol and water. Pure acetaldehyde is recovered by distillation, and an additional column is used to separate ethanol for recycle from higher-boiling products. It may not be necessary to supply pure aldehdye to the α-hydroxysulfonic acid process above and the crude stream may suffice. The hydrogen-rich off-gas is suitable for hydrogenation reactions or can be used as fuel to supply some of the endothermic heat of the ethanol dehydrogenation reaction. The copper-based catalyst has a life of several years but requires periodic regeneration. In an oxidation process, ethanol maybe converted to acetaldehyde in the presence of air or oxygen and using a silver catalyst in the form of wire gauze or bulk crystals. Typically, the reaction is carried out at temperatures between 500° and 600° C., depending on the ratio of ethanol to air. Part of the acetaldehyde is also formed by dehydrogenation, with further combustion of the hydrogen to produce water. At a given reaction temperature, the endothermic heat of dehydrogenation partly offsets the exothermic heat of oxidation. Ethanol conversion per pass is typically between 50 and 70%, and the selectivity to acetaldehyde is in the range of 95 to 97 mol %. By-products include acetic acid, $CO$ and $CO_2$. The separation steps are similar to those in the dehydrogenation process, except that steam is generated by heat recovery of the reactor effluent stream. The off-gas steam consists of nitrogen containing some methane, hydrogen, carbon monoxide and carbon dioxide; it can be used as lean fuel with low calorific value. An alternative method to produce acetaldehyde by air oxidation of ethanol in the presence of a Fe—Mo catalyst. The reaction can be carried out at about 180-240° C. and atmospheric pressure using a multitubular reactor. According to patent examples, selectivities to acetaldehyde between 95 and 99 mol % can be obtained with ethanol conversion levels above 80%.

Figure 1:
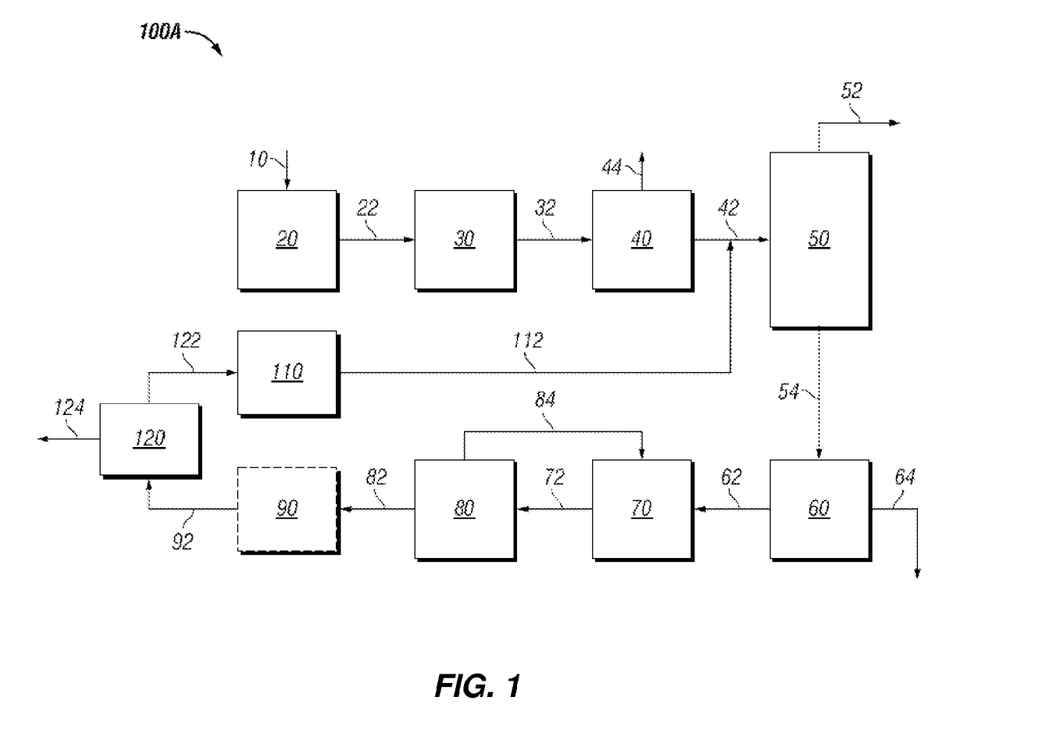
FIG. 1 schematically illustrates a block flow diagram of an embodiment of the treatment process of this invention.
Figure 2:
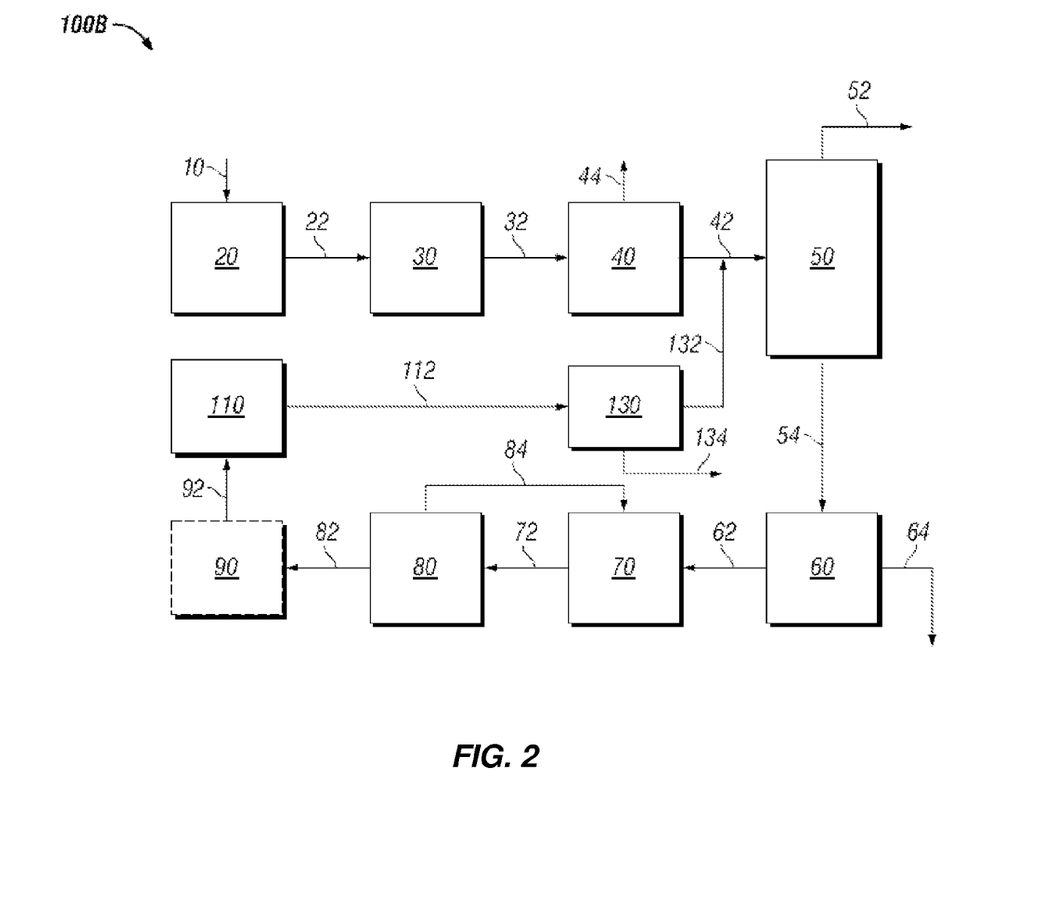
FIG. 2 schematically illustrates a block flow diagram of another embodiment of the treatment process of this invention.

In some embodiments, the reactions described below are carried out in any system of suitable design, including systems comprising continuous-flow (such as CSTR and plug flow reactors), batch, semi-batch or multi-system vessels and reactors and packed-bed flow-through reactors. For reasons strictly of economic viability, it is preferable that the invention is practiced using a continuous-flow system at steady-state equilibrium. The ease of acid removal in the process invention, in contrast to typical mineral acid pretreatments, represents a particular advantage. Thus, the process of the invention results in potentially less expensive processing systems by eliminating subsequent acid neutralization steps and salt formations. The present process provides a method of producing sugars and/or alcohols from wet distiller's grains or stillage. FIG. 1 and FIG. 2 show an embodiment of the present invention 100A or 100B for converting WDG into fermentable sugars then additional alcohols. In these embodiments, a grain feedstock 10 is subjected to a grinding (or milling) 20 producing flour 22. The flour is then treated 30 to produce a fermentable sugar mixture 32.

In a typical treatment step, the ground grain (flour) is mixed with water and the starch is converted into sugars by reaction with enzymes in numerous possible configurations known to those in the art and described in, for example, W. M. Ingledrew, D. R, Kelsall, G. D. Austin, C. Kluhspies, The Alcohol Textbook, Fifth Edition, Nottingham University Press, Nottingham, UK, 2009. In a typical ethanol production, two main enzymes assist in the catalytic breakdown of the starch to glucose. The first is the endoenzyme α-amylase, which acts to breaking the α-1,4 glycosidic linkage of the starch to produce oligosaccharides of varying molecular weights called "dextrins". The breakdown of dextrins is usually performed in the fermentor using a second enzyme, glycozmylases (amyloglucosidase) which hydrolyses the dextrins to glucose monomers which are fermentable sugars. In one embodiment, the treatment process involves cooking/liquifaction with a slurry tank (mush "mingler") where ground grain is mixed with water (may be recycled) and hydrolyzing in the presence of enzymes to produce fermentable sugars such as glucose. The process may involve cooking or depending on the enzyme cold-cook where the hydrolysis is conducted at fermentation temperature or no-cook where enzyme is stirred below the gelatinization temperature of the starch. This treatment step may be conducted in a batch process, continues or semi-continuous process.

Yeast is added to the fermentable sugar mixture to convert the sugars to ethanol and carbon dioxide in the fermentation process 40, thereby producing (first) fermented products 42 containing about 15% ethanol, solids from the grain, and water and carbon dioxide 44 that can be removed or captured. The fermentation process in 40 employs typical fermentive organisms that convert the hexose sugars to ethanol. The fermented product is then separated to produce ethanol and residue (stillage) in a distillation process 50. The distillation can be conducted in a multi-column distillation system with additional heat input into the system. In the process, ethanol 52 can be separated (that maybe further concentrated) and the stillage 54 that contains solids and water that is removed from the bottom of the column. The stillage can be separated in a step 60 into thin stillage 64 (a liquid with 5-10% solids) and wet distillers grain 62. The separation may be carried out, for example, by decanting, centrifuge or any other methods that can conveniently separate the liquid from solids. A portion of the thin stillage can be routed back to the cooking process as makeup water (not shown), reducing the amount of fresh water required by the cook process. The wet distillers grain is introduced into a hydrolysis reaction 70 to produce at least one fermentable sugar containing product 72. In the hydrolysis reaction may comprise a number of components including α-hydroxysulfonic acid added or generated in situ. The term "in situ" as used herein refers to a component that is produced within the overall process; it is not limited to a particular reactor for production or use and is therefore synonymous with an in process generated component. The reacted product stream 72 from 70 is introduced to acid removal system 80 where the acid is removed in its component form then is recovered (and optionally scrubbed) either as components or in its recombined form and recycled via recycle stream 84 to 70 and product stream 82 containing at least one fermentable sugar (e.g., pentose and optionally hexose) substantially free of the alpha-hydroxysulfonic acids is produced for further processing. The product stream 82 optionally may be further processed by enzyme hydrolysis process 90 thereby providing a hydrolyzate 92. In FIG. 1, the product stream 92 is optionally clarified 120 by removing the solids 124 from the product stream to produce enhanced wet distiller grains and a liquid product stream 122. The liquid product stream is then treated by a C5/C6 fermentation process 110 fermenting the hydrolyzate thereby providing a (second) fermentation product 112 that can subsequently be combined with the first fermentation product for distillation 50. In the C5/C6 fermentation process, an microorganism capable of fermenting both C5 and C6 sugar is used due to the presence of higher concentration of C5 sugars in the C5/C6 fermentation process 110 then fermentation process 40. In FIG. 2, instead of clarification of the product stream 92, the second fermentation product 112 is clarified 130 to remove solids (enhanced wet distiller grains) 134. The product stream 82 may be directly provided to the C5/C6 fermentation process 110 which contains fermentive organisms that will convert both the contained pentose and hexose sugars to ethanol.

Figure 3:
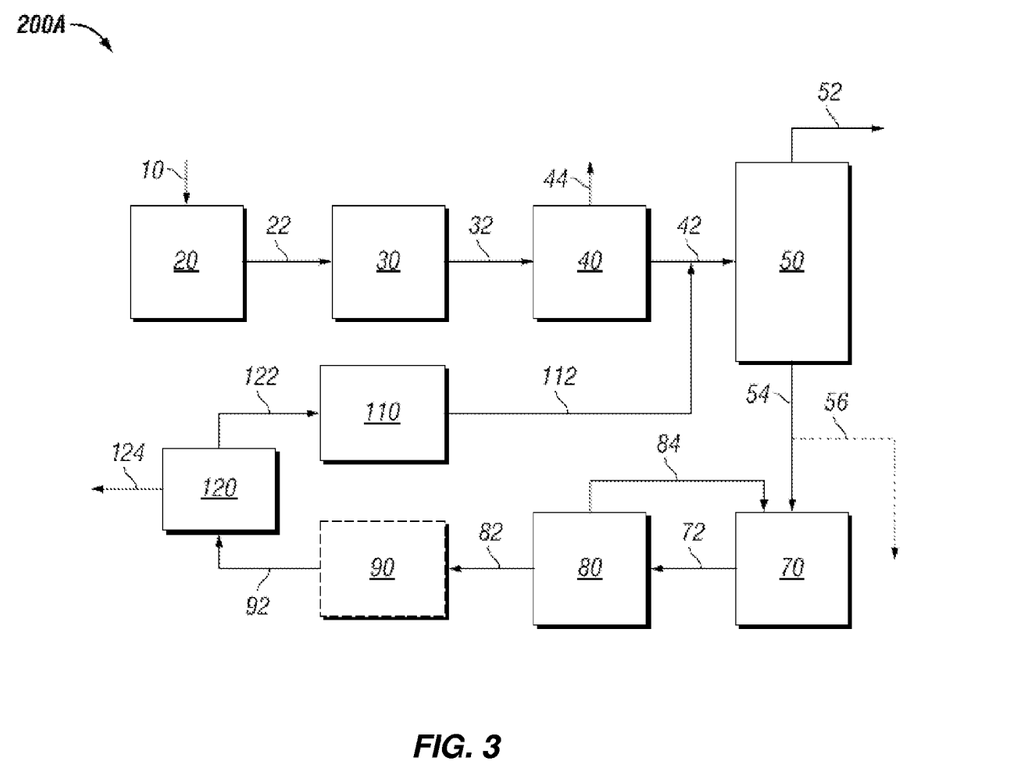
FIG. 3 schematically illustrates a block flow diagram of another embodiment of the treatment process of this invention.
Figure 4:
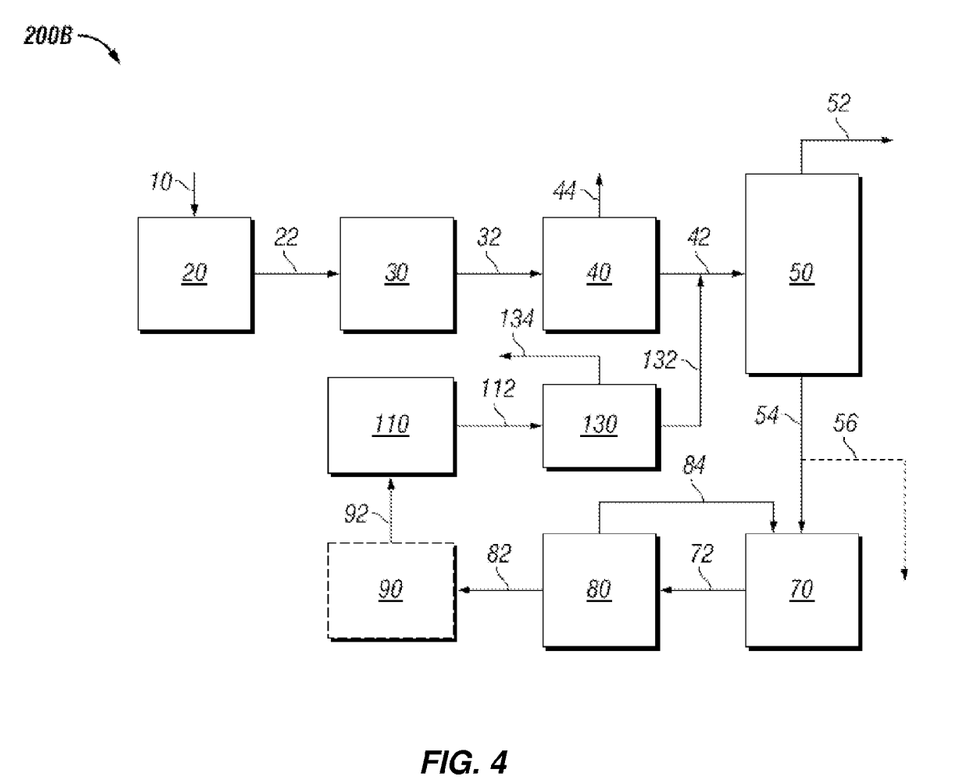
FIG. 4 schematically illustrates a block flow diagram of another embodiment of the treatment process of this invention

FIGS. 3 and 4 show another embodiment of the present invention 200A or 200B for converting WDG into fermentable sugars then additional alcohols. In these embodiments, a grain feedstock 10 is subjected to a grinding (or milling) 20 producing flour 22. The flour is then treated 30 to produce a fermentable sugar mixture 32. A typical treatment step that may include cooking/liquefaction and hydrolysis to produce fermentable sugar mixture is described above.

Yeast is added to the fermentable sugar mixture to convert the sugars to ethanol and carbon dioxide in the fermentation process 40, thereby producing (first) fermented products 42 containing about 15% ethanol, solids from the grain, and water and carbon dioxide 44 that can be removed or captured. The fermentation process in 40 employs typical fermentive organisms that convert the hexose sugars to ethanol. The fermented product is then separated to produce ethanol and residue (stillage) in a distillation process 50. The distillation can be conducted in a multi-column distillation system with additional heat input into the system. In the process, ethanol 52 can be separated (that maybe further concentrated) and the stillage 54 that contains solids and water that is removed from the bottom of the column. At least a portion of the stillage is directly introduced into a hydrolysis reaction 70 to produce at least one fermentable sugar containing product 72. In the hydrolysis reaction may comprise a number of components including in situ generated α-hydroxysulfonic acid. The term "in situ" as used herein refers to a component that is produced within the overall process; it is not limited to a particular reactor for production or use and is therefore synonymous with an in process generated component. The reacted product stream 72 from 70 is introduced to acid removal system 80 where the acid is removed in its component form then is recovered (and optionally scrubbed) either as components or in its recombined form and recycled via recycle stream 84 to 70 and product stream 82 containing at least one fermentable sugar (e.g., pentose and/or hexose) substantially free of the alpha-hydroxysulfonic acids is produced for further processing. The product stream 82 optionally may be further processed by enzyme hydrolysis process 90 thereby providing a hydrolyzate 92. In FIG. 3, the product stream 92 is optionally clarified 120 by removing the solids 124 from the product stream to produce enhanced wet distiller grains and a liquid product stream 122. The liquid product stream is then treated by a C5/C6 fermentation process 110 fermenting the hydrolyzate thereby providing a (second) fermentation product 112 that can subsequently be combined with the first fermentation product for distillation 50. In the C5/C6 fermentation process, an microorganism capable of fermenting both C5 and C6 sugar is used due to the presence of higher concentration of C5 sugars in the C5/C6 fermentation process 110 then fermentation process 40. In FIG. 4, instead of clarification of the product stream 92, the second fermentation product 112 is clarified 130 to remove solids (enhanced wet distiller grains) 134. The product stream 82 may be directly provided to the C5/C6 fermentation process 110 which contains fermentive organisms that will convert both the contained pentose and hexose sugars to ethanol.

It is also contemplated that at least a portion of the product containing fermentable sugar from 72 or 82, after solids removal, can be directly passed to the fermentation process 40 (not shown in FIG. 1 or FIG. 2) without the need for a separate enzyme hydrolysis process 90 and fermentation process 110.

Various factors affect the conversion of the WDG or stillage in the hydrolysis reaction. The carbonyl compound or incipient carbonyl compound (such as trioxane) with sulfur dioxide and water should be added to in an amount and under conditions effective to form alpha-hydroxysulfonic acids. The temperature and pressure of the hydrolysis reaction should be in the range to form alpha-hydroxysulfonic acids and to hydrolyze WDG or stillage into pentoses and/or hexoses. The amount of carbonyl compound or its precursor and sulfur dioxide or its precursor should be to produce alpha-hydroxysulfonic acids (or recombined) in the range from about 1 wt %, preferably from about 5 wt %, most preferably from about 10 wt %, to about 55 wt %, preferably to about 50 wt %, more preferably to about 40 wt %, based on the total solution. For the reaction, excess sulfur dioxide is not necessary, but any excess sulfur dioxide may be used to drive the equilibrium in eq. 1 to favor the acid form at elevated temperatures. The contacting conditions of the hydrolysis reaction may be conducted at temperatures preferably at least from about 50° C. depending on the alpha-hydroxysulfonic acid used, although such temperature may be as low as room temperature depending on the acid and the pressure used. The contacting condition of the hydrolysis reaction may range preferably up to and including about 150° C. depending on the alpha-hydroxysulfonic acid used. In a more preferred condition the temperature is at least from about 80° C., most preferably at least about 100° C. In a more preferred condition the temperature range up to and including about 90° C. to about 120° C. The reaction is preferably conducted at as low a pressure as possible, given the requirement of containing the (free) sulfur dioxide. The reaction may also be conducted at a pressure as low as about 1 barg, preferably about 4 barg, to about pressure of as high as up to 10 barg The temperature and pressure to be optimally utilized will depend on the particular alpha-hydroxysulfonic acid chosen and optimized based on economic considerations of metallurgy and containment vessels as practiced by those skilled in the art.

The amount of acid solution to "dry weight" biomass (WDG or solids in stillage) determines the ultimate concentration of fermentable sugar obtained. Thus, as high a biomass concentration as possible is desirable. This is balanced by the absorptive nature of biomass with mixing, transport and heat transfer becoming increasingly difficult as the relative amount of biomass solids to liquid is increased. Numerous methods have been utilized by those skilled in the art to circumvent these obstacles to mixing, transport and heat transfer. Thus weight percentage of biomass solids to total liquids (consistency) may be as low as 1% or as high as 33% or even higher depending on the apparatus chosen and the nature of the biomass.

The temperature of the hydrolysis reaction can be chosen so that the maximum amount of extractable carbohydrates are hydrolyzed and extracted as fermentable sugar from the WDG or stillage while limiting the formation of degradation products.

In some embodiments, a plurality of reactor vessels may be used to carry out the hydrolysis reaction. These vessels may have any design capable of carrying out a hydrolysis reaction. Suitable reactor vessel designs can include, but are not limited to, batch, trickle bed, co-current, counter-current, stirred tank, or fluidized bed reactors. Staging of reactors can be employed to arrive the most economical solution. The remaining WDG or stillage solids may then be optionally separated from the liquid stream to allow more severe processing of the recalcitrant solids or pass directly within the liquid stream to further processing that may include enzymatic hydrolysis, fermentation, extraction, distillation and/or hydrogenation. In another embodiment, a series of reactor vessels may be used with an increasing temperature profile so that a desired sugar fraction is extracted in each vessel. The outlet of each vessel can then be cooled prior to combining the streams, or the streams can be individually fed to the next reaction for conversion.

The treatment reaction product contains fermentable sugar or monosaccharides, such as pentose and/or hexose that is suitable for further processing. The residual alpha-hydroxysulphonic acid can be removed by application of heat and/or vacuum from the fermentable sugar containing product stream to reverse the formation of alpha-hydroxysulphonic acid to its starting material to produce a stream containing fermentable sugar substantially free of the α-hydroxysulfonic acid. In particular, the product stream is substantially free of alpha-hydroxysulphonic acid, meaning no more than about 2 wt % is present in the product stream, preferably no more than about 1 wt %, more preferably no more than about 0.2 wt %, most preferably no more than about 0.1 wt % present in the product stream. The temperature and pressure will depend on the particular alpha-hydroxysulphonic acid used and minimization of temperatures employed are desirable to preserve the sugars obtain in treatment reactions. Typically the removal may be conducted at temperatures in the range from about 50° C., preferably from about 80° C., more preferably from 90, to about 110° C., up to about 150° C. The pressure in the range of from about 1 bara (atmospheric), to about 3 bara, more preferably from 1 bara to about 2 bara. It can be appreciated by a person skill in the art that the treatment reaction 70 and the removal of the acid 80 can occurred in the same vessel or a different vessel or in a number of different types of vessels depending on the reactor configuration and staging as long as the system is designed so that the reaction is conducted under condition favorable for the formation and maintenance of the alpha-hydroxysulfonic acid and removal favorable for the reverse reaction. As an example, the reaction in the reactor vessel 70 can be operated at approximately 100° C. and a pressure of 4 barg in the presence of alpha-hydroxyethanesulfonic acid and the removal vessel 80 can be operated at approximately 110° C. and a pressure of 0.5 barg. It is further contemplated that the reversion can be favored by the reactive distillation of the formed alpha-hydroxysulfonic acid. In the recycling of the removed acid, optionally additional carbonyl compounds, $SO_2$, and water may be added as necessary. The removed starting material and/or alpha-hydroxysulphonic acid can be condensed or scrubbed by contact with water and recycled as a recycle stream 84 to the reaction 70.

Thus, a typical reaction mixture contains (a) WDG and/or stillage, (b) at least one α-hydroxysulfonic acid, and (c) water. Once some of the WDG and/or stillage is hydrolyzed the reaction mixture contains (a) WDG and/or stillage, (b) at least one α-hydroxysulfonic acid (c) water, and (d) at least one fermentable sugar.

In one embodiment, the cellulose containing product stream can further be optionally hydrolyzed by other methods, for example by enzymes to further hydrolyze the product stream to additional sugar products containing fermentable sugar (e.g., glucose) and fermented to produce alcohols such as disclosed in US Publication No. 2009/0061490 and U.S. Pat. No. 7,781,191 which disclosures are hereby incorporated by reference.

In yet another embodiment, the fermentable sugar can be converted to furfural or further fermented to alcohols. Although in some embodiments it may be desirable to minimize the formation of furfural, if formation of furfural is desired, the acid containing solution may be further heated to a temperature in the range of from 110 to 160° C., more preferably in the range of from 120 to 150° C. to form a furfural containing product stream. In one embodiment, the temperature of such step is maintained to a temperature of 100° C. or less if it is desirable to obtain minimal furfural in the product stream.

In yet another embodiment, the fermentable sugars can be converted to higher hydrocarbons as a biofuel component using catalytic hydrogenation and condensation techniques (not shown) rather than further hydrolysis by enzyme and fermentation. Typically, the fermentable sugar containing product stream is contacted with hydrogen in the presence of a hydrogenolysis catalyst to form a plurality of oxygenated intermediates, and then further processing the oxygenated intermediates to produce a fuel blend in one or more processing reactions. In an embodiment, a condensation reaction can be used along with other reactions to generate a fuel blend and may be catalyzed by a catalyst comprising acid or basic functional sites, or both to product a liquid fuel. As used herein, the term "higher hydrocarbons" refers to hydrocarbons having an oxygen to carbon ratio less than at least one component of the WDG or stillage feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (e.g., oxygen or sulfur) and thus the term "hydrocarbon" may also include substituted hydrocarbons.

In one such example, the fermentable sugar containing product stream 72 or 82 may be further processed to produce mixtures of C4+ compounds useful for biofuels such as described in U.S. Publication Nos. US2011/0154721 and US2011/0282115 which disclosures are hereby incorporated by reference. As another such example, the fermentable sugar containing product stream 72 or 82 may be further processed to produce mixtures of C4+ compounds useful for biofuels such as described in U.S. Publication No. 20080216391 which disclosure is hereby incorporated by reference. The solid feed may also be suitable for use in fast pyrolysis reactions leading to fuels and chemicals.

The term "fermentable sugar" refers to oligosaccharides and monosaccharides that can be used as a carbon source (e.g., pentoses and hexoses) by a microorganism in a fermentation process. It is contemplated that fermentable sugar may be fermented as described above, but may also be processed by other methods without fermentation to produce fuels as described above. The term "pentose" refers to monosaccharides with five carbon atoms. The term "hexose" refers to monosaccharides with six carbon atoms.

In an enzymatic hydrolysis-fermentation processes the pH of the pretreated feedstock to the enzymatic hydrolysis is typically adjusted so that it is within a range which is optimal for the cellulase enzymes used. Generally, the pH of the pretreated feedstock is adjusted to within a range of about 3.0 to about 7.0, or any pH there between.

If the optional enzyme hydrolysis step is desired for further fermentable sugar production, the temperature of the treated feedstock is adjusted so that it is within the optimum range for the activity of the cellulase enzymes. Generally, a temperature of about 15° C. to about 100° C., about 20° C. to about 85° C., about 30° C. to about 70° C. preferably or any temperature there between, is suitable for most cellulase enzymes. The cellulase enzymes and the β-glucosidase enzyme are added to the pretreated feedstock, prior to, during, or after the adjustment of the temperature and pH of the aqueous slurry after pretreatment. Preferably the cellulase enzymes and the β-glucosidase enzyme are added to the pretreated lignocellulosic feedstock after the adjustment of the temperature and pH of the slurry.

By the term "cellulase enzymes" or "cellulases," it is meant a mixture of enzymes that hydrolyze cellulose. The mixture may include cellobiohydrolases (CBH), glucobiohydrolases (GBH), endoglucanases (EG), and β-glucosidase. By the term "β-glucosidase", it is meant any enzyme that hydrolyzes the glucose dimer, cellobiose, to glucose. In a non-limiting example, a cellulase mixture may include EG, CBH, and β-glucosidase enzymes.

The enzymatic hydrolysis may also be carried out in the presence of one or more xylanase enzymes. Examples of xylanase enzymes that may also be used for this purpose and include, for examples, xylanase 1, 2 (Xyn1 and Xyn2) and β-xylosidase, which are typically present in cellulase mixtures.

The process can be carried out with any type of cellulase enzymes, regardless of their source. Non-limiting examples of cellulases which may be used include those obtained from fungi of the genera *Aspergillus*, *Humicola*, and *Trichoderma*, *Myceliophthora*, *Chrysosporium* and from bacteria of the genera *Bacillus*, *Thermobifida*, and *Thermotoga*. In some embodiments, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

The cellulase enzyme dosage is chosen to convert the cellulose of the pretreated feedstock to glucose. For example, an appropriate cellulase dosage can be about 0.1 to about 40.0 Filter Paper Unit(s) (FPU or IU) per gram of cellulose, or any amount there between. The term Filter Paper Unit(s) refers to the amount of enzyme required to liberate 2 mg of reducing sugar (e.g., glucose) from a 50 mg piece of Whatman No. 1 filter paper in 1 hour at 50° C. at approximately pH 4.8.

In practice, the hydrolysis may carried out in a hydrolysis system, which may include a series of hydrolysis reactors. The number of hydrolysis reactors in the system depends on the cost of the reactors, the volume of the aqueous slurry, and other factors. The enzymatic hydrolysis with cellulase enzymes produces an aqueous sugar stream (hydrolyzate) comprising glucose, unconverted cellulose, lignin and other sugar components. The hydrolysis may be carried out in two stages (see U.S. Pat. No. 5,536,325, which is incorporated herein by reference), or may be performed in a single stage.

In the fermentation system, the aqueous sugar stream is then fermented by one or more than one fermentation microorganism to produce a fermentation broth comprising the alcohol fermentation product useful as biofuels. In the fermentation system, any one of a number of known microorganisms (for example, yeasts or bacteria) may be used to convert sugar to ethanol or other alcohol fermentation products. The microorganisms convert sugars, including, but not limited to glucose, mannose and galactose present in the clarified sugar solution to a fermentation product.

Many known microorganisms can be used in the present process to produce the desired alcohol for use in biofuels. *Clostridia*, *Escherichia coli* (*E. coli*) and recombinant strains of *E. coli*, genetically modified strain of *Zymomonas mobilis* such as described in US2003/0162271, 60/847,813 and 60/847,856 (which disclosures are herein incorporated by reference) are some examples of such bacteria. The microorganisms may further be a yeast or a filamentous fungus of a genus *Saccharomyces*, *Kluyveromyces*, *Candida*, *Pichia*, *Schizosaccharomyces*, *Hansenula*, *Kloeckera*, *Schwanniomyces*, *Yarrowia*, *Aspergillus*, *Trichoderma*, *Humicola*, *Acremonium*, *Fusarium*, and *Penicillium*. The fermentation may also be performed with recombinant yeast engineered to ferment both hexose and pentose sugars to ethanol. Recombinant yeasts that can ferment one or both of the pentose sugars xylose and arabinose to ethanol are described in U.S. Pat. No. 5,789,210, U.S. Pat. No. 6,475,768, European Patent EP 1,727,890, European Patent EPI 863,901 and WO 2006/096130 which disclosures are herein incorporated by reference. Xylose utilization can be mediated by the xylose reductase/xylitol dehydrogenase pathway (for example, WO9742307 A1 19971113 and WO9513362 A1 19950518) or the xylose isomerase pathway (for example, WO2007028811 or WO2009109631) It is also contemplated that the fermentation organism may also produce fatty alcohols, for example, as described in WO 2008/119082 and PCT/US07/011923 which disclosure is herein incorporated by reference. In another embodiment, the fermentation may be performed by yeast capable of fermenting predominantly C6 sugars for example by using commercially available strains such as *Thermosacc* and *Superstart*.

Preferably, the fermentation is performed at or near the temperature and pH optima of the fermentation microorganism. For example, the temperature may be from about 25° to about 55° C., or any amount there between. The dose of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The fermentation may be conducted in batch, continuous or fed-batch modes, with or without agitation. The fermentation system may employ a series of fermentation reactors.

In some embodiment, the hydrolysis system and fermentation system may be conducted in the same vessel. In one embodiment, the hydrolysis can be partially completed and the partially hydrolyzed stream may be fermented. In one embodiment, a simultaneous saccharification and fermentation (SSF) process where hydrolysis system may be run until the final percent solids target is met and then the hydrolyzed biomass may be transferred to a fermentation system.

The fermentation system produces an alcohol stream preferably containing at least one alcohol having 2 to 18 carbon atoms. In the recovery system, when the product to be recovered in the alcohol stream is a distillable alcohol, such as ethanol, the alcohol can be recovered by distillation in a manner known to separate such alcohol from an aqueous stream. If the product to be recovered in the alcohol stream is not a distillable alcohol, such as fatty alcohols, the alcohol can be recovered by removal of alcohols as solids or as oils from the fermentation vessel, thus separating from the aqueous effluent stream.

While the invention is susceptible to various modifications and alternative forms, specific embodiments thereof are shown by way of examples herein described in detail. It should be understood, that the detailed description thereto are not intended to limit the invention to the particular form disclosed, but on the contrary, the intention is to cover all modifications, equivalents and alternatives falling within the spirit and scope of the present invention as defined by the appended claims. The present invention will be illustrated by the following illustrative embodiment, which is provided for illustration only and is not to be construed as limiting the claimed invention in any way.

ILLUSTRATIVE EMBODIMENTS

General Methods and Materials

In the examples, the aldehyde or aldehyde precursors and sulfur dioxide were obtained from Sigma-Aldrich Co.

Wet distillers grain from a corn mill operation was obtained via commercial sources in Hereford, Tex. The material was analyzed for content using standard TAPPI methods (T-249, T-211) on rinsed material. The wet distillers grain was rinsed by slurrying 150 grams of the wet solids with two 200 ml portions of water, isolating the solids via centrifugation. The rinsed material had the following average composition on a dry basis:

| | |
|---|---|
| Glucan (and starch) | 19.7 wt. % |
| Xylan | 9.1 wt. % |
| Arabinan | 5.4 wt. % |
| Galactan | 1.4 wt. % |
| Mannan | 2.0 wt. % |
| Uronic Acid | 0.8 wt. % |
| Ash | 1.7 wt. % |
| Other (Protein, lignin, oil | 59.9 wt. % |

Analytical Methods
Determination of Oxygenated Components in Aqueous Layer.

A sample or standard is analyzed by injection into a stream of a mobile phase that flows though a Bio-rad column (Aminex HPX-87H, 300 mm×7.8 mm) The reverse phase HPLC system (Shimadzu) equipped with both RI and UV detectors and the signals are recorded as peaks on a data acquisition and data processing system. The components are quantified using external calibration via a calibration curves based on injection of know concentrations of the target components. Some of the components were calculated by using single point of standard. The reference samples contained 0.5% Glucose, Xylose and Sorbitol in water HPLC Instrument Conditions:
    Column: Bio-Rad Aminex HPX-87H (300 mm×7.8 mm)
    Flow Rate: 0.6 ml/minute
    Column Oven: 30° C.
    Injection Volume: 10 μl
    UV Detector: @320 NM
    RI Detector: mode—A; range—100
    Run Time: 70 minute
    Mobile Phase: 5 mM Sulfuric Acid in water
    Sample is either injected directly or diluted with water first, but makes sure there is no particulars. Pass through the 0.2 μm syringe filter, if there is precipitation in the sample or diluted sample. Samples were analyzed for Glucose, Xylose, Cellobiose, Sorbitol, Formic Acid, Acetic Acid, Arabinose, hydroxymethyl furfural, and Furfural content.

EXAMPLES

General Procedure for the Formation of α-Hydroxysulfonic Acids

Aldehydes and ketones will readily react with sulfur dioxide in water to form α-hydroxy sulfonic acids according to the equation 1 above. These reactions are generally rapid and somewhat exothermic. The order of addition ($SO_2$ to carbonyl or carbonyl to $SO_2$) did not seem to affect the outcome of the reaction. If the carbonyl is capable of aldol reactions, preparation of concentrated mixtures (>30% wt.) are best conducted at temperatures below ambient to minimize side reactions. We have found it beneficial to track the course of the reaction using in situ Infrared Spectroscopy (ISIR) employing probes capable of being inserted into pressure reaction vessels or systems. There are numerous manufacturers of such systems such as Mettler Toledo Autochem's Sentinal probe. In addition to being able to see the starting materials: water (1640 $cm^{-1}$), carbonyl (from approx. 1750 $cm^{-1}$ to 1650 $cm^{-1}$ depending on the organic carbonyl structure) and $SO_2$ (1331 $cm^{-1}$), the formation of the α-hydroxysulfonic acid is accompanied by the formation of characteristic bands of the $SO_3^-$ group (broad band around 1200 $cm^{-1}$) and the stretches of the α-hydroxy group (single to multiple bands around 1125 cm$^{-1}$). In addition to monitoring the formation of the α-hydroxy sulfonic acid, the relative position of the equilibrium at any temperature and pressure can be readily assessed by the relative peak heights of the starting components and the acid complex. The definitive presence of the α-hydroxy sulfonic acid under biomass hydrolysis conditions can also be confirmed with the ISIR and it is possible to monitor the growth of sugars in the reaction mixture by monitoring the appropriate IR bands.

Example 1

Formation of 40% Wt. α-Hydroxyethane Sulfonic Acid from Acetaldehyde

Into a 2 liter C-276 Parr autoclave fitted with DiComp IR optics was added 1346.1 grams of ice cold nitrogen degassed aqueous solution containing 17.96% wt. of acetaldehyde. The top was place on the reactor and the vessel was connected to two single ended Hoke vessels charged with a total of 362.04 grams of sulfur dioxide. The sealed reactors pressure integrity was ensured by a 15 minute test at 50 psig with nitrogen gas. The reactor was cooled to less than 5° C. using external chilling and the nitrogen cap was vented. The IR acquisition was initiated followed several minutes later by injection of the sulfur dioxide from the attached Hoke vessels to the acetaldehyde/water solution. The pressure in the reactor spiked to approximately 3 bar and then rapidly dropped to atmospheric pressure as the ISIR indicated the appearance and then rapid consumption of the SO$_2$. The temperature of the reaction mixture rose approximately 42° C. during the formation of the acid (from 3° C. to 45° C.). ISIR and reaction pressure indicated the reaction was complete in approximately 10 minutes. The final solution showed an infrared spectrum with the following characteristics: a broad band centered about 1175 cm$^{-1}$ and two sharp bands at 1038 cm$^{-1}$ and 1015 cm$^{-1}$. The reaction mixture was cooled to room temperature and the atmosphere contained vented through a caustic scrubber. The reactor was purged to remove any unreacted SO$_2$ or acetaldehyde by two cycles of pressurization with nitrogen to 50 psig and then venting. This produced 1698.78 g of a mixture that was analyzed via proton NMR to contain 39.3% wt. α-hydroxyethanesulfonic acid.

Example 2

Formation of 40% wt. α-Hydroxyethane Sulfonic Acid from Metaldehdye

Into a 2 liter C-276 Parr autoclave fitted with DiComp IR optics was added 999.98 grams of nitrogen degassed water and 212.02 g of metaldehyde (water insoluble). The vessel head was attached and to this was connected to two single ended Hoke vessels charged with a total of 338.19 grams of sulfur dioxide. The reactor was sealed and the pressure integrity was confirmed by a 15 minute test at 100 psig with nitrogen gas. The nitrogen cap was vented very slowly to prevent any loss of free metaldehyde not wetted by the water. Stirring was initiated at 1000 rpm and the IR acquisition was begun. After 5 minutes the sulfur dioxide from the attached Hoke vessels was added to the metaldehyde/water slurry. The pressure in the reactor spiked to approximately 2.5 bar. ISIR indicated the appearance of the SO$_2$. The temperature of the reaction mixture was slowly increased to 30° C. then incrementally by 10° C. to 50° C. During transition from 40 to 50° C. the reaction temperature abruptly rose to 65° C. and the ISIR indicated formation of HESA. This was accompanied by the consumption of SO$_2$ and a fall in the reactor pressure. ISIR of the reaction mixture indicated the reaction was complete within a few minutes. The final solution showed an infrared spectrum with the following characteristics: a broad band centered about 1175 cm$^{-1}$ and two sharp bands at 1038 cm$^{-1}$ and 1015 cm$^{-1}$. The reaction mixture was cooled to room temperature and the atmosphere contained vented through a caustic scrubber. The reactor was purged to remove any unreacted SO$_2$ or acetaldehyde by two cycles of pressurization with nitrogen to 50 psig and then venting. This produced 1468.74 g of a light yellow homogeneous liquid that was analyzed via proton NMR to contain 36.7% wt. α-hydroxyethanesulfonic acid.

Examples 3 through 7

Figure 5:
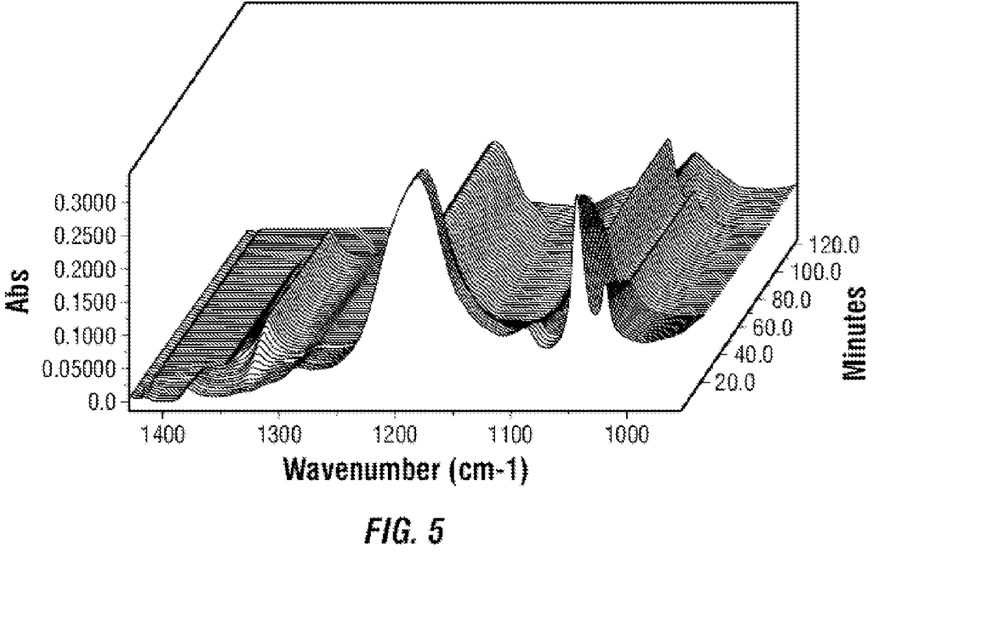
FIG. 5 shows a three dimensional IR plot, plotting individual IR spectra over time from the treatment of wet distillers grain with 9% wt. α-hydroxyethane sulfonic acid at 110° C. followed by reversion of the acid.
Figure 6:
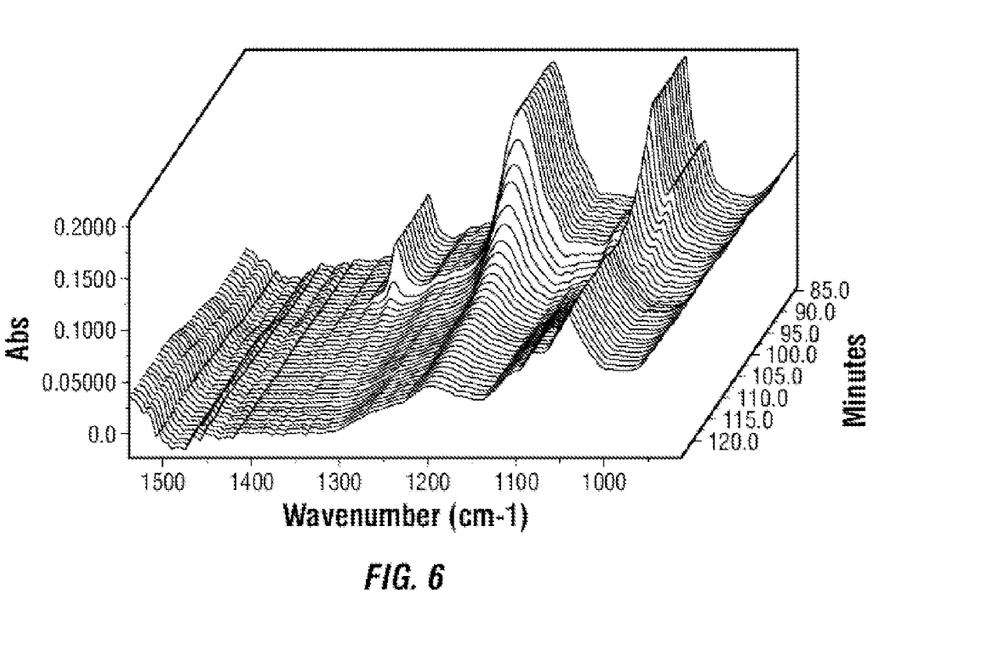
FIG. 6 shows a three dimensional IR plot, plotting the individual IR spectra over time at the end of a reaction period through the reversal of the α-hydroxyethanesulfonic acid (HESA) at 100° C. via reduction in pressure while maintaining temperature.

Hydrolysis of Wet Distillers Grain with α-Hydroxyethane Sulfonic Acid (HESA) Solutions This is the general procedure for examples 3 through 7. Into a 300 ml autoclave equipped with a DiComp IR probe place approximately 50 grams of WDG as obtained (wet, unrinsed, dry wt. basis is recorded in column B). To this add approximately 120 grams of a 8 to 20% wt. HESA solution (exact concentration listed in column C) at room temperature. The reactor was sealed with a top containing a magnetically coupled 4 blade down pitch impeller, fitted with heating bands and purged by adding nitrogen to 50 psig followed by venting to room temperature. The reaction mixture is heated to the target temperature of 100 to 120° C. (column D) with stirring (column E) and held at temperature the requisite time (column F). During this period of time the in situ IR reveals the presence of HESA, SO$_2$, and acetaldehyde in an equilibrium mixture and a growth in bands characteristic of the sugars grew in around 1000 cm$^{-1}$ (as shown in FIG. 5). At the end of the reaction period the acid reversal was accomplished via opening the gas cap of the reactor to an overhead condensation system for recovery of the acid while maintaining the reactor temperature at 100° C. This overhead recovery system was a ¼" C-267 tube that extends downward into a 250 ml three neck round bottom flask charged with 70 grams of DI water, immersed in a wet ice bath and fitted with a dry ice/acetone condenser on the outlet. The progress of the acid reversion was monitored via the use of in situ IR in the Parr reactor. The reversal was continued until the in situ IR of the Parr reactor contents showed no remaining traces of the α-hydroxyethane sulfonic acid or SO$_2$ in the reaction mixture (FIG. 6). The reactor was then sealed and cooled to room temperature. The overhead condensate contained >85% of the HESA charged to the system as analyzed by proton NMR in all cases (column G). The cooled reactor was opened and the contents filtered through a medium glass frit funnel using a vacuum aspirator to draw the liquid through the funnel. The reactor was rinsed with three separate portions of water, noting weight on all rinses, rinses being used to complete the transfer of solids and rinse the solids in the funnel. The residual solid was dried to a constant weight in the air and then analyzed for moisture (the recovered weight on a dry basis in listed in column H). HPLC analysis of the filtrate plus rinses was used to obtain the results of hydrolysis (columns I to K).

TABLE 1

| A Example | B WDG (g) dry wt. basis | C [HESA] % wt. | D React. Temp. (° C.) | E Stirrer Speed (RPM) | F React. Time (hr) | G HESA recovered (mole %) | H Solids recovered (g) dry wt. basis | I Glucose (g) in filtrate | J Xylose (g) in Filtrate | K Arabinose (g) in Filtrate | L Furfural (g) in Filtrate |
|---|---|---|---|---|---|---|---|---|---|---|---|
| 3 | 18.0 | 9.1 | 110 | 1500 | 1 | 95.3 | 6.24 | 2.23 | 1.88 | 1.07 | 0.003 |
| 4 | 18.0 | 9.3 | 120 | 1500 | 1 | 86.6 | 3.14 | 2.28 | 1.83 | 1.01 | 0.006 |
| 5 | 18.0 | 17.9 | 100 | 1500 | 1 | 86.0 | 4.17 | 2.38 | 2.03 | 1.16 | 0.004 |
| 6 | 18.0 | 8.9 | 100 | 1500 | 0.5 | 91.5 | 8.42 | 1.36 | 1.60 | 1.00 | 0.004 |
| 7 | 20.0 | 10.0 | 100 | 1000 | 1 | 88.3* | 9.35 | 1.89 | 1.61 | 0.90 | 0.007 |

*HESA not fully reverted (2.73 mole % of original acid left in reactor

What is claimed is:

1. A method of treating ethanol production byproduct comprising: (a) providing a wet distillers grain containing moisture; (b) contacting the wet distillers grain with a solution comprising at least one α-hydroxysulfonic acid thereby hydrolyzing the wet distillers grain to produce at least one fermentable sugar containing product; and (c) removing at least a portion of said α-hydroxysulfonic acid in its component form from said fermentable sugar containing product by a process consisting of heating and/or reducing pressure to produce an acid-removed product containing at least one fermentable sugar.

2. The method of claim 1, further comprising recycling the removed α-hydroxysulfonic acid obtained in step (c) to step (b) as components or in its recombined form.

3. The method of claim 1, further comprising fermenting said acid-removed product to produce at least one alcohol.

4. The method of claim 1, further comprising hydrolyzing said acid-removed product to produce a hydrolyzed product.

5. The method of claim 4, further comprising fermenting said hydrolyzed product to produce at least one alcohol.

6. The method of claim 1, wherein said α-hydroxysulfonic acid is present in an amount of 1% wt. to 55% wt., based on the solution.

7. The method of claim 1, wherein said α-hydroxysulfonic acid is produced from a carbonyl compound or a precursor to a carbonyl compound combined with sulfur dioxide and water.

8. The method of claim 1, wherein said α-hydroxysulfonic acid is in-situ generated.

9. The method of claim 1, wherein step (b) is carried out at a temperature within the range of 50° C. to 150° C. and a pressure within the range of 1 barg to 10 barg.

10. A method comprising: (a) providing grain; (b) grinding said grain to produce ground grain; (c) treating said ground grain to produce a fermentable sugar mixture; (d) fermenting the fermentable sugar mixture to produce a fermented product containing ethanol, solids and water; (e) separating said fermented product to produce ethanol and stillage containing water; (f) contacting at least a portion of said stillage containing water with a solution comprising at least one α-hydroxysulfonic acid thereby hydrolyzing said stillage to produce at least one fermentable sugar containing product; and (g) removing at least a portion of said α-hydroxysulfonic acid in its component form from said fermentable sugar containing product by a process consisting of heating and/or reducing pressure to produce an acid-removed product containing at least one fermentable sugar.

11. The method of claim 10, further comprising recycling the removed α-hydroxysulfonic acid obtained in step (g) to step (f) as components or in its recombined form.

12. The method of claim 10, further comprising fermenting said acid-removed product to produce at least one alcohol.

13. The method of claim 10, further comprising hydrolyzing said acid-removed product to produce a hydrolyzed product.

14. The method of claim 13, further comprising fermenting said hydrolyzed product to produce at least one alcohol.

15. The method of claim 10, wherein said α-hydroxysulfonic acid is present in an amount of 1% wt. to 55% wt., based on the solution.

16. The method of claim 10, wherein said α-hydroxysulfonic acid is produced from a carbonyl compound or a precursor to a carbonyl compound combined with sulfur dioxide and water.

17. The method of claim 10, wherein said α-hydroxysulfonic acid is in-situ generated.

18. The method of claim 10, wherein step (f) is carried out at a temperature within the range of 50° C. to 150° C. and a pressure within the range of 1 barg to 10 barg.

19. A method comprising: (a) providing grain; (b) grinding said grain to produce ground grain; (c) treating said ground grain to produce fermentable sugar mixture; (d) fermenting said fermentable sugar mixture to produce a fermented product containing ethanol, solids and water; (e) separating said fermented product to produce ethanol and stillage; (f) separating said stillage to produce thin stillage and wet distillers grain containing moisture; and (g) contacting at least a portion of said wet distillers grain containing moisture with a solution comprising at least one α-hydroxysulfonic acid thereby hydrolyzing said wet distillers grain to produce at least one fermentable sugar containing product; and (h) removing at least a portion of said α-hydroxysulfonic acid in its component form from said fermentable sugar containing product by a process consisting of heating and/or reducing pressure to produce an acid-removed product containing at least one fermentable sugar.

20. The method of claim 19, further comprising recycling the removed α-hydroxysulfonic acid obtained in step (h) to step (g) as components or in its recombined form.

21. The method of claim 19, further comprising fermenting said acid-removed product to produce at least one alcohol.

22. The method of claim 19, further comprising hydrolyzing said acid-removed product to produce a hydrolyzed product.

23. The method of claim 22, further comprising fermenting said hydrolyzed product to produce at least one alcohol.

24. The method of claim 19, wherein said α-hydroxysulfonic acid is present in an amount of 1% wt. to 55% wt., based on the solution.

25. The method of claim 19, wherein said α-hydroxysulfonic acid is produced from a carbonyl compound or a precursor to a carbonyl compound combined with sulfur dioxide and water.

26. The method of claim 19, wherein said α-hydroxysulfonic acid is in-situ generated.

27. The method of claim 19, wherein step (g) is carried out at a temperature within the range of 50° C. to about 150° C. and a pressure within the range of 1 barg to 10 barg.

\* \* \* \* \*